United States Patent
Lechner et al.

(10) Patent No.: US 9,562,871 B2
(45) Date of Patent: Feb. 7, 2017

(54) INTEGRATED CHEMICAL SENSOR CHIP

(71) Applicant: Sensirion AG, Stafa (CH)

(72) Inventors: Moritz Lechner, Uerikon (CH);
Samuel Fuhrer, Richterswil (CH);
Zeljko Mrcarica, Zurich (CH);
Ferdinando Pace, Birmensdorf (CH);
Leo Zimmerman, Wilen B. Wollerau (CH)

(73) Assignee: Sensirion AG, Stafa (CH)

( * ) Notice: Subject to any disclaimer, the term of this patent is extended or adjusted under 35 U.S.C. 154(b) by 0 days.

(21) Appl. No.: 14/826,697

(22) Filed: Aug. 14, 2015

(65) Prior Publication Data
US 2016/0077031 A1 Mar. 17, 2016

(30) Foreign Application Priority Data

Sep. 15, 2014 (EP) ..................................... 14003186

(51) Int. Cl.
| | |
|---|---|
| *G01N 7/00* | (2006.01) |
| *G01N 21/00* | (2006.01) |
| *G01N 27/00* | (2006.01) |
| *G01N 31/00* | (2006.01) |
| *G01N 33/00* | (2006.01) |

(Continued)

(52) U.S. Cl.
CPC ............ *G01N 27/16* (2013.01); *G01N 27/124* (2013.01); *G01N 27/128* (2013.01); *G01N 33/0008* (2013.01); *G01N 33/0009* (2013.01); *H04M 2250/12* (2013.01)

(58) Field of Classification Search
CPC ........ G01N 15/06; G01N 33/00; G01N 33/48; G01N 7/00; G01N 21/00; G01N 27/00; G01N 31/00

USPC ...... 422/50, 68.1, 502, 503, 504, 83, 88, 98; 436/43
See application file for complete search history.

(56) References Cited

U.S. PATENT DOCUMENTS

| | | |
|---|---|---|
| 5,528,225 A | 6/1996 | Sakai et al. |
| 5,898,101 A | 4/1999 | Lyle et al. |
| 7,010,391 B2 * | 3/2006 | Handique et al. ............ 700/266 |

(Continued)

FOREIGN PATENT DOCUMENTS

| | | |
|---|---|---|
| EP | 2762881 | 8/2014 |
| EP | 2763381 | 8/2014 |

(Continued)

OTHER PUBLICATIONS

Alan Richard Wilson et al., "Network Low-Power Sensing: Network Interface and Main Operating System", IEEE Sensors Journal, vol. 10, No. 9, Sep. 2010.

(Continued)

*Primary Examiner* — Brian J Sines
(74) *Attorney, Agent, or Firm* — Cooper & Dunham LLP

(57) ABSTRACT

An integrated chemical sensor chip comprises on or integrated in a common substrate a chemically sensitive layer and a heater heating the sensitive layer. In addition, a memory is provided for the storage of a measurement routine, the measurement routine comprising instructions defining a heating process over time and instructions defining one or more measurement points in time. An I/O interface is provided for receiving a trigger for the measurement routine and for supplying a result of the measurement routine. An engine controls the heater and measures a resistance of the sensitive layer according the instructions of the measurement routine.

12 Claims, 6 Drawing Sheets

(51) Int. Cl.
*G01N 27/16* (2006.01)
*G01N 27/12* (2006.01)

(56) References Cited

U.S. PATENT DOCUMENTS

| | | | |
|---|---|---|---|
| 7,192,557 B2* | 3/2007 | Wu et al. | 422/81 |
| 7,635,594 B2* | 12/2009 | Holmes et al. | 436/50 |
| 8,012,744 B2* | 9/2011 | Gibbons et al. | 435/288.5 |
| 8,088,593 B2* | 1/2012 | Burd et al. | 435/7.92 |
| 8,088,616 B2* | 1/2012 | Handique | 435/287.2 |
| 2002/0152791 A1 | 10/2002 | Cardinale | |
| 2005/0101250 A1 | 5/2005 | Helal et al. | |
| 2012/0270611 A1 | 10/2012 | Choi et al. | |
| 2014/0076022 A1 | 3/2014 | Ohisson et al. | |
| 2014/0223995 A1 | 8/2014 | Buhler et al. | |

FOREIGN PATENT DOCUMENTS

| | | |
|---|---|---|
| EP | 2763468 | 8/2014 |
| JP | 6148116 | 5/1994 |
| JP | 200724508 | 8/2008 |

OTHER PUBLICATIONS

Anland D. Mane et al., "Explosive Detection with Mobile Telephony an Attempt Towards a Safe Ambience", Proceedings of 2011 International Conference on Signal Processing, Communication, Computing and Networking Technolgies (ICSCCN 2011), pp. 187-191.

Michael Karst et al. "Humidity & Temperature Sensors in Mobile Phones", Sensirion AG, Switzerland, Apr. 18, 2012.

Section 41. 32-Bit Programmable Cyclic Redundancy Check (CRC), 2009 Microchip Technology Inc., DS39729A, pp. 41-1-41-22.

Alireza Shoa et al., "Run-Time Reconfigurable Systems for Digital Signal Processing Applications: A Survey", Journal of VLSI Signal Processing 39, pp. 213-235, 2005.

D. Weiler et al., "An Absolute Air Pressure Smart Sensor Family with 2 Dimensional Calibration", Fraunhofer Institute of Microelectronic Circuits and Systems (IMS)., pp. 254-257.

* cited by examiner

INTEGRATED CHEMICAL SENSOR CHIP

CROSS REFERENCE TO RELATED APPLICATION

This application claims priority of European Patent Application 14003186.5, filed Sep. 15, 2014, the contents of which is incorporated herein by reference in its entirety.

FIELD OF THE INVENTION

The present invention relates to an integrated chemical sensor chip, particularly a gas sensor chip, and to a method for conducting a measurement with an integrated chemical sensor chip.

BACKGROUND OF THE INVENTION

Metal-oxide chemical sensors are based on the concept that gaseous analytes interact with a metal oxide sensitive layer at elevated temperatures of the sensitive layer in the range of more than 100° Celsius, and specifically between 250° C. and 350° Celsius. As a result of a catalytic reaction, a conductivity of the sensitive layer may change which change can be measured. Hence, such chemical sensors are also denoted as high temperature chemoresistors for the reason that a chemical property of the analyte is converted into an electrical resistance at high temperatures of the sensitive layer.

A chemical sensor can be a gas sensor for detecting one or more substances in a gas, and specifically in the air surrounding a portable multi-purpose electronic device such a mobile phone or a tablet computer. Hence, in a sample application it may be of interest to identify, if such air may contain analytes the chemical sensor is tuned to detect. Specific applications may include the detection of toxic gases, the detection of ethanol, sulphide compounds or other components in a user's breath, or the detection of other substances.

It is also known to arrange such a chemical sensor inside a housing of a portable electronic device, such as a mobile phone, for example. An opening may be provided in the housing for exposing the chemical sensor to a fluid to be analyzed.

It is seen as particular problem to adapt a multitasking CPU of such a portable electronic device to the specific control requirements for a chemical sensor. It can be very difficult to provide instructions for a CPU to maintain control of the chemical sensor's operations while the same CPU is tasked to control core functions such as data and voice communication. The steps required to prepare a chemical sensor for a measurement as well as the actual measurement typically happen on a timescale of several seconds. The processing units in portable electronic devices, however, are often not suited to maintain control of a process for durations exceeding one second.

In the light of the above, it is therefore seen as an object of the invention to improve a chemical sensor and a method for operating a chemical sensor that particularly is suited for mounting into the housing of a portable multi-purpose electronic device.

SUMMARY OF THE INVENTION

Hence, according to a first aspect of the invention, there is provided an integrated chemical sensor chip, comprising on or integrated in a common substrate a chemically sensitive layer, a heater for heating the sensitive layer, a memory for the storage of a measurement routine, the measurement routine comprising instructions defining a heating process over time and instructions defining one or more measurement points in time, an I/O interface for receiving a trigger for the measurement routine and for supplying a result of the measurement routine, and an engine for controlling the heater and measuring a resistance of the sensitive layer according the instructions of the measurement routine in response to a trigger for the measurement routine.

The integrated chemical sensor chip—also referred to as sensor chip—preferably comprises a semi-conductor substrate, and preferably a silicon substrate, and layers thereon such as insulation and/or metal layers, for integrating circuitry. The chemically sensitive layer—also referred to as sensitive layer—is arranged on or is integrated in the layers or the substrate. It is noted that the term "arranged on the substrate" shall include both a direct arrangement on a surface of the substrate and an indirect arrangement on the substrate with one or more layers in between. The sensitive layer is sensitive to one or more analytes, also referred to as substances or compounds, for example in a gas the sensor chip may be exposed to. In a preferred embodiment, the sensitive layer comprises a metal-oxide material that gaseous analytes interact with at elevated temperatures of the sensitive layer, e.g. in the range of more than 100° Celsius, and specifically between 250° C. and 350° Celsius. As a result of a catalytic reaction, a conductivity of the sensitive layer may change which change is measured. Applications of the integrated chemical sensor chip may include the detection of one or more of toxic gases, ethanol, sulphide compounds or other components in a user's breath, or the detection of other substances.

For heating the sensitive layer, the sensor chip comprises a heater, e.g. a resistive heater which generates heat upon the application of an electric current. The sensor chip further contains an integrated on-chip memory, which on-chip memory preferably is a non-volatile memory, and preferably is an at least one-time programmable memory. In the memory chip, a measurement routine is stored—which measurement routine is also referred to as profile—comprising instructions defining a heating process over time and instructions defining one or more measurement points in time. The measurement routine preferably is stored in the memory in form of a macro. An engine is provided in the sensor chip for controlling the heater and for measuring a resistance of the sensitive layer according to the instructions of the measurement routine. Preferably, the engine is hardwired in the integrated chemical sensor chip. And preferably, the sensor chip comprises a system controller configured to copy the instructions of the measurement routine stored in the memory into registers of the engine for execution.

The nature of the chemical sensor chip may require a defined course of heating and a defined course of measuring over time. Taking a measurement typically is far more complex than defining one heating temperature and one measuring point in time. Points in time when measurements are due are typically synchronized with the heating activities. In view of this, it is preferred, that the heating process as well as the measurement points in time are defined by absolute time stamps with respect to the beginning of the measurement routine. Preferably, in the measurement routine a heating sub-process for heating to one defined temperature is programmed in combination with the relevant points in time for measurements during this particular heating sub-process. Hence, the profile comprises a heating profile or a temperature profile variable of time. A heating profile may indicate the heating power to be applied over time e.g. in an open loop control, whereas the temperature profile may indicate the temperature of the sensitive layer—or a membrane the sensitive layer is arranged on—to be achieved, a temperature of which may be measured by a temperature sensor such that the heater may be controlled in a closed loop by comparing the measured temperature to the actual value of the temperature profile. The profile further comprises a measuring profile, which sets the points in time a measurement is to be taken. Hence, the measuring routine relies on being controlled in real-time, and may require a rather long control period, e.g. in the order of one second or more. This control period is owed to thermal processes involved as well as to chemical processes. The thermal processes which result in heating times to be controlled are dependent on a thermal time constant of the membrane the heater preferably resides on or in, but may also be impacted by circuitry that controls the heating power and drives the heater. The definition of the points in time a measurement is taken in turn may be defined by the number of measurands taken per time point, by circuitry for the taking of the measurements—e.g. parallel measurements or sequential measurements to reuse the circuitry—and/or by noise requirements, e.g. low-pass filtering to eliminate noise. Further, the measurement routine preferably is to be run in an asynchronous mode, preferably interrupt controlled.

Hence, a one chip solution is suggested which preferably is built as an asynchronous system, wherein a processing in the engine causes an interrupt at the system controller. The system controller—which is not a microprocessor—accepts the interrupt and invokes another processing activity in the engine. Hence, the internal processes are not visible from the perspective of the profile. On the other hand, profile commands and internal chip activities are synchronized without the need for an external microprocessor or software.

This in turn gives the following advantages:

The system is made tolerant for multiple processes at different time constants, even for time constants that are not exactly known when the chip is designed, and tolerant for e.g. chemical time constants that are even not exactly known when the measurement routine is programmed in the form of one or multiple macros. Such chemical time constants, e.g. in form of reaction times, may be in the range of 100 ms to multiple seconds, while a thermal time constant of the membrane may be in the range of 1 ms to 20 ms. Digital or analogue parts of the sensor chip instead may show time constants in the nanosecond or microsecond range, e.g. digital delays, RC delays, clock, etc.

The power consumption is small enough such that a heating of the chip invoked by the on-chip system controller and the engine remains insignificant, and in particular does not impact on-chip signal processing, does not impact a thermal behavior of the membrane, and does not impact a chemical reaction rate near the membrane. On the other hand, the power consumption of the chemical sensor chip is small enough to make the sensor chip fit into mobile applications, and in particular into modern communication devices such as smart phones, etc., as is the footprint of the chemical sensor chip. In addition, different measurement routines can be stored in the memory which makes the chemical sensor chip flexible for different use cases. For example, measurement profiles can be stored which distinguish in at least one of a heating/temperature profile, a resolution of time, or a number of measurements. If only a single use case is implemented and a single measurement routine is stored in the memory, the footprint of the on-chip memory can be reduced, which footprint may even further be reduced when no memory needs to be provided for storing intermediate measurement results in case the amount of data measured is low and can immediately be transferred via the I/O interface.

The I/O interface may not only be used for supplying measurement results but also for receiving a trigger for a measurement routine. Hence, when the sensor chip is linked to a processing unit, e.g. of a portable electronic device, and in particular to a non-real-time operating processing unit, the processing unit can trigger a measurement routine via the I/O interface, and the sensor chip returns measurement results to the processing unit via this I/O interface. In this respect, the sensor chip can be considered as a black box from an application point of view in the portable electronic device. However, the measurement routine may not only be triggerable by the processing unit but also may be triggerable by the sensor chip itself in a standalone mode.

The present architectural approach enables a chemical sensor measurement in particular in mobile communication devices such as mobile phones or tablet computers given that general purpose communication CPUs of such devices—and even dedicated application processing units or dedicated sensor hub processing units—do not offer the capabilities of controlling long-lasting processes in real-time in an asynchronous manner.

On the other hand, adding a full scale microprocessor for the execution of the measurement routine would be counterproductive in view many aspects: Additional footprint would be required. In addition, a dedicated microprocessor is considered to consume too much power which is not desired in portable electronic devices. In case of integrating a full scale microprocessor on the sensor chip itself, another fundamental drawback would occur: The heat lost by such microprocessor would impact the measurement where defined temperature levels are required as is explained above. In this context, it is noted that the currently known processing units in portable electronic device are further not configured to upload code such as a measurement routine would be required to be uploaded.

Instead, in an embodiment of the present invention, it is only one or more measurement routines stored in an on-chip memory, an engine for executing the related heating and measurement processes, and possibly a system controller for controlling a system bus on the sensor chip that are needed for conducting a measurement. Such hardware is much less footprint intense and much less power consuming compared to a microprocessor implementation.

The system controller of the sensor chip preferably is understood as control unit for on-chip operations and hence has a reduced instruction set compared to a microprocessor. In one embodiment, the system controller operates—and preferably is limited to operating—an on-chip system bus and copies data thereto and fetches data therefrom. No main memory is required. In another embodiment, no bus architecture is provided and but the system controller is connected to the elements such as the memory and the engine point-to-point.

The engine preferably contains hardwired registers. In one embodiment, the engine solely operates on registers, busses and timers. Preferably, the engine is granted access to the relevant memory addresses upon the system controller copying the content/instruction of the starting address of the measurement routine to an engine register. If required by the engine, measurement values may be received by the system controller copying such measurement value from a dedicated register via the system bus to a register of the engine. If required by the engine, a temperature value stored in the memory is copied by the system controller from the memory to the engine via the system bus. A corresponding heating to such temperature may then be executed by the engine.

Summarizing, instructions preferably representing a macro are stored in the memory and are executed by on-chip logic in the engine to heat the heater, to take measurements, and to execute timers. The macro preferably contains a sequence of instructions required for heating and measuring synchronized with the heating. An execution of these instructions may be triggered by receiving a macro command which is associated with a memory address where the corresponding instructions start in the memory. In this context, it may be preferred to have various measurement routines stored in the memory which may be represented by different macros. This provides flexibility in that various use cases also in terms of the detection of different chemical substances can be implemented in the same hardware.

In a preferred embodiment, the engine in combination with the system controller and with instructions stored in the memory may perform further processing of a sensor signal of the sensitive layer, such as linearization, calibration, temperature and/or humidity compensation, etc.

Preferably, a portable electronic device, comprises an integrated chemical sensor chip according to any one of the above embodiments, in addition to a processing unit, such as one or more of a central processing unit, an application processing unit or a sensor hub processing unit. Preferably the processing unit comprises an I/O interface for communicating with the integrated chemical sensor chip, is configured to send a trigger for a measurement routine via the I/O interface to the integrated chemical sensor chip, and is configured to receive a result of the measurement routine via the I/O interface. This processing unit of the portable electronic device preferably is a non-real-time processing unit. Preferably, the portable electronic device comprises a housing with the processing unit and the chemical sensor chip being arranged in the common housing, which in one embodiment could e.g. be the housing of a smartphone, and preferably wherein the chemical sensor chip sufficiently is exposed to the ambient for detecting chemical substances of the ambient. In a preferred embodiment, the portable electronic device comprises a common carrier for the chemical sensor chip and the processing unit, wherein the common carrier may, for example, be a circuit board such as a PCB. Preferably, the portable electronic device is one of a mobile phone, a handheld computer, an electronic reader, a tablet computer, a game controller, a pointing device, a photo or a video camera, a digital music player, an electronic wrist watch, a personal health tracking device, a headset, or a computer peripheral.

According to another aspect of the present invention, a method is provided for conducting a measurement in an integrated chemical sensor chip. A trigger is received for conducting a measurement routine. In response to the trigger, a heater of the sensor chip is controlled according to instructions stored in a memory of the sensor chip defining a heating process over time. In addition, and preferably concurrently with the heating, a resistance of a chemically sensitive layer of the sensor chip is measured according to instructions stored in a memory defining one or more measurement points in time. Finally, a result of the measuring is supplied.

It is noted that embodiments described in relation to one category of claims shall be considered as disclosed in connection with the one or more other category, too.

Other advantageous embodiments are listed in the dependent claims as well as in the description below.

BRIEF DESCRIPTION OF THE FIGURES

The embodiments defined above and further aspects, features and advantages of the present invention can also be derived from the examples of embodiments to be described hereinafter and are explained with reference to the drawings. In the drawings the figures illustrate in FIG. 1A an integrated chemical sensor chip according to an embodiment of the invention as shown in a perspective view.

DETAILED DESCRIPTION OF THE FIGURES

Figure 1A:
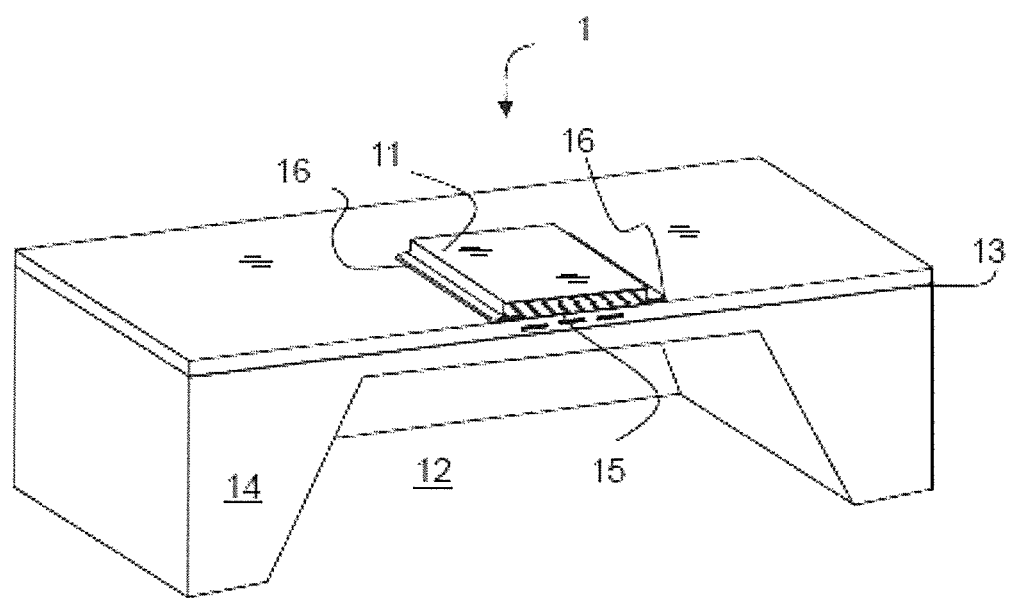
FIG. 1B an integrated chemical sensor chip according to an embodiment of the invention as shown in a cut through of a portion.
Figure 1B:
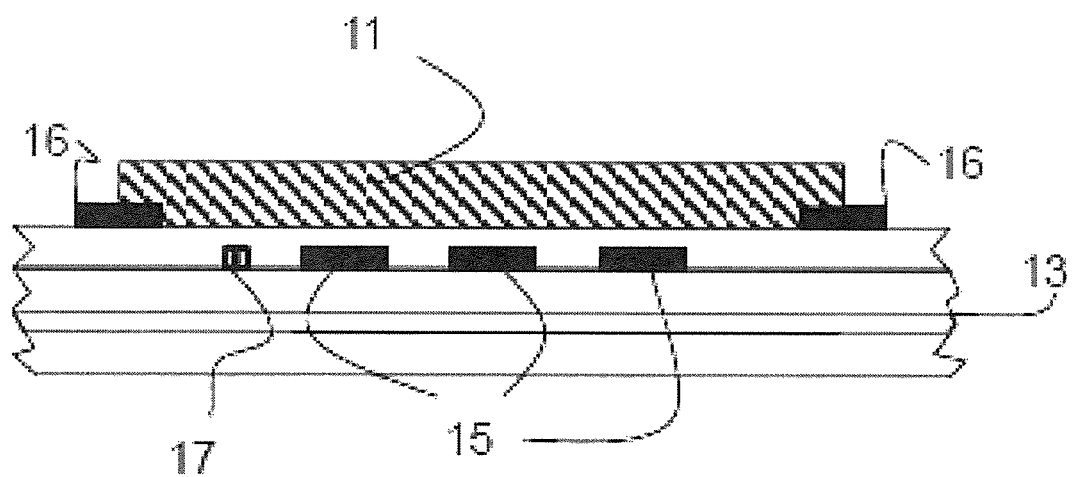

FIG. 1 illustrates an integrated chemical sensor chip 1 in a perspective view in diagram A, and in a cut through of a portion in diagram B. The sensor chip 1 comprises a sensing layer 11 of metal oxide. The sensor chip 1 is integrated with a CMOS circuitry (not shown) which CMOS circuitry encompasses at least a memory, a system controller, an engine for performing a measurement routine stored in the memory, and other circuitry. Layers 13, e.g. CMOS layers, and a substrate 14, such as a silicon substrate contribute to the CMOS circuitry. A portion of the substrate 14, and possibly a portion of the layers 13 are etched away to form a cavity 12 at a location where the chemically sensitive layer 11 is arranged. The chemically sensitive layer 11 preferably comprises metal oxide material and is sensitive to one or more gas compounds. The (remaining) layers 13 on top of the cavity 12 therefore form a thin membrane to support the sensitive layer 11.

Embedded within the layers 13 are conducting elements forming a heater 15 to provide a local source of heat to heat the metal oxide sensitive layer 11 during operation of the sensor chip 1. In response to heating the heater 15, the membrane acts as a hot plate and temperature can rise rapidly around the metal oxide sensitive layer 11, while the thicker part of the sensor chip 1 reacts due to its thermal inertia with a slower rise of temperature. By controlling the heater 15 accordingly, a chemical reaction in the vicinity of the hotplate can be activated, which can be detected by the metal oxide sensitive layer 11.

The metal oxide sensitive layer 11 is contacted by two conductive electrodes 16 and hence acts as a resistor. In the presence of an analyte this resistance changes thereby providing a measure of the concentration of the analyte in the immediate vicinity of the metal oxide sensitive layer 11.

Typically an additional temperature sensor 17 may be integrated on or into the membrane for measuring a temperature thereof. A polycrystalline silicon (poly-Si) or a metal resistor can be used as temperature sensor, for example.

Figure 2:
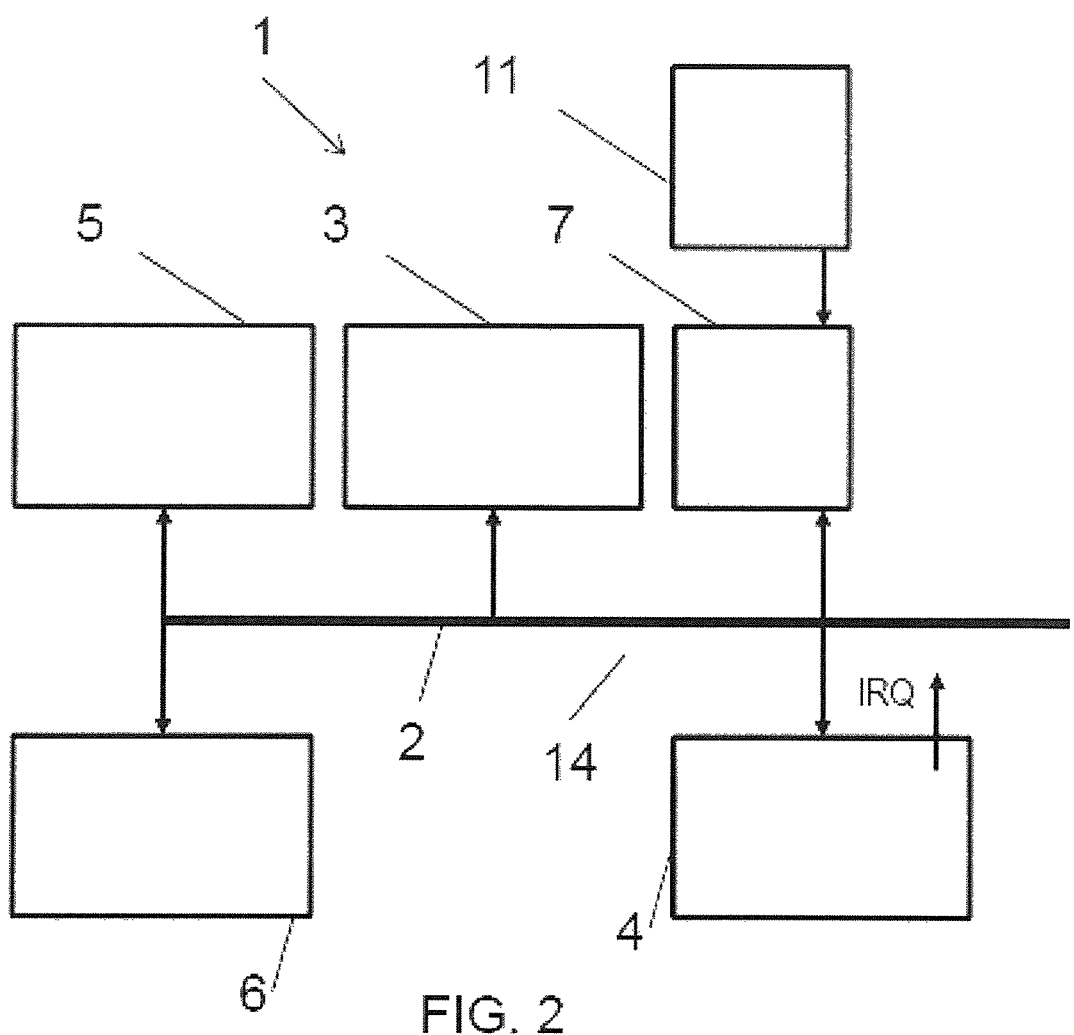
FIG. 2 a block diagram of an integrated chemical sensor chip according to an embodiment of the invention.

FIG. 2 illustrates a block diagram of an integrated chemical sensor chip according to an embodiment of the present invention. The sensor chip 1 contains a bus 2 which interconnects various elements of the sensor chip 1. In another variant, no bus is provided. Instead, the elements are connected point-to-point where needed. In the present embodiment, an at least one-time programmable on-chip memory 3 is provided and connected to the bus 2. An analogue to digital converter ADC 7 converts an analogue sensor signal of a chemically sensitive layer 11 into digital sensor values. In the on-chip memory 3, one or more macros are stored each macro representing a measurement routine. An engine 4 is provided for executing the instructions representing a macro. The engine 4 is implemented in hardwired logic and preferably comprises registers for executing operations. Preferably, the engine 4 provides only hardwire logic for adding values in registers, and one or more timers, and is incapable of executing higher order operations such as multiplications etc.

A system controller 5 is provided for copying an instruction from a memory address to the engine 4 which memory address indicates a start of the macro in the space of the memory 3. By receiving this instruction, the engine 4 gets access to the on-chip memory 3 and may start executing the subsequent instructions in its hardwired logic.

In one embodiment, the system controller 5 may fetch a heating temperature value from an address of the memory 3 and copy it into a register of the engine 4 for further operation according to the measurement routine. The engine 4 may accordingly apply a current through the heater 5. In another embodiment, the system controller 5 may fetch a sensor signal value from a register of the analogue to digital converter 7 and may copy such value in a register of the engine 4 for further operation according to the measurement routine. Finally, an output value may be determined as a result of the measurement routine and be stored to a register of the engine 4, wherefrom the system controller 5 may pick it up and transfer to an I/O interface 6, such as an I²C interface, to make this processed output value available to the outside of the sensor chip.

In this embodiment, a data flow from and to the engine 4 is controlled entirely by the system controller 5 which reacts on interrupt requests IRQ by the engine 4, except, e.g. where there is a dedicated interface between the engine 4 and the on-chip memory 3 in order to reduce the workload on the bus 2.

Figure 3:
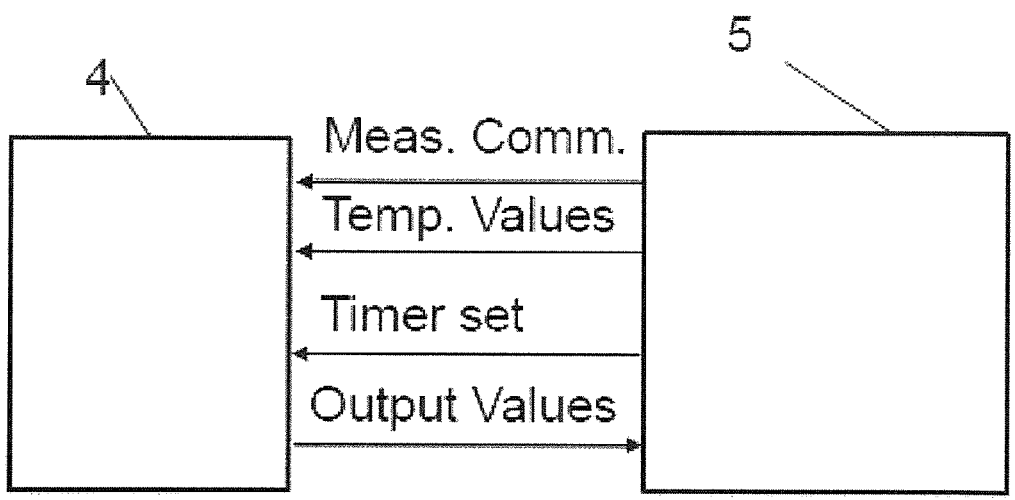
FIG. 3 flow of information between two building blocks of an integrated chemical sensor chip according to an embodiment of the present invention.

FIG. 3 illustrates a flow of information between two building blocks of an integrated chemical sensor chip according to an embodiment of the present invention, i.e. between the engine 4 of FIG. 2, and the system controller 5 of FIG. 2. First, in response to a trigger received via the I/O interface 6, a memory address is identified by the system controller in the on-chip memory 3 at which address the desired measurement routine starts at. The instruction stored at this starting address is copied to the engine 4 and executed there. In the course of the execution of the macro, measurement commands, heating temperatures, or settings of timers may be copied to the engine 4 for being executed there. In turn, the engine 4 may supply output values, for example. When the engine 4 has determined an output value, this output value is copied by the system controller 5 to the on-chip memory 5, or is copied to the I/O interface 6.

Figure 4:
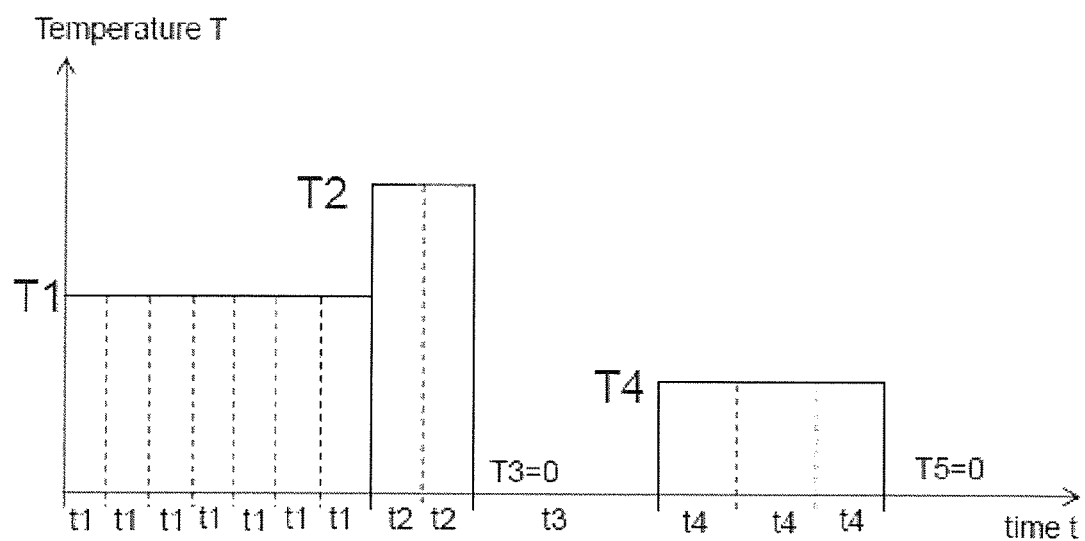
FIG. 4 a sample measurement routine as stored in a memory of an integrated chemical sensor chip according to an embodiment of the present invention.

FIG. 4 illustrates the timing aspects of a sample measurement routine, also referred to as a profile over time. In general, the profile comprises a heating or temperature profile, which indicates heating power to be applied to the heater, or temperatures to be achieved at the sensitive layer respectively, as a variable of time. The profile further comprises a measuring profile, which sets the points in time measurements are taken.

A sample profile is shown in FIG. 4 in a temperature T over time t chart. Accordingly, the sensitive layer is heated at t=0 to temperature T1 and remains at T1 for 7*t1, before the temperature is raised to T2 and stays there for 2*t2. The heater is switched off (T3=0) for t3, before the heater is switched on again such the sensitive layer achieves temperature value T4 for 3*t4. Then, the heater is switched off again. The straight vertical lines in the diagram show, at which points in time heat instructions shall be executed. In contrast, the dashed vertical lines indicate, at which points in time measurements are taken, collectively building the measuring profile. In chemical sensing with metal oxide sensitive layers, a relative timing of heating the sensitive layer and taking measurements is crucial for getting reliable results.

The profile can be described by a syntax applied per heating section, such as e.g. for the heating section T1:

| 0x0001 | //T1 | *Temperature T1* |
| 0x0040 | //t1 | *time step t1 = 5ms* |
| 0x0005 | //5 | *repeated 6 times* |

The profile preferably is translated in instructions in form of a macro defining the heating/temperature process over time and instructions defining the measurement points in time.

Figure 5:
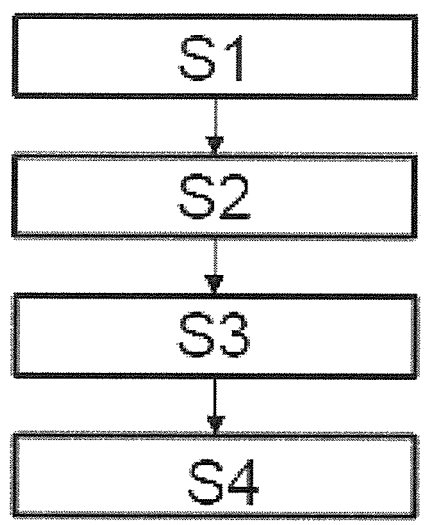
FIG. 5 a flowchart of a method according to an embodiment of the present invention.

FIG. 5 shows a flowchart of a method according to an embodiment of the present invention. The steps are executed by an integrated chemical sensor chip according to an embodiment of the present invention.

In step S1, a trigger is received requesting for conducting a measurement routine. In response to the trigger, in step S2 a heater of the sensor chip is controlled according to instructions stored in a memory of the sensor chip defining a heating process over time, In step S2, a resistance of a chemically sensitive layer of the sensor chip is measured at defined time points in relation to the heating activities, again according to instructions stored in the memory defining the one or more measurement points in time. In step S3, a measurement result such as a measured value may be processed, e.g. by applying calibration parameters to the measured value. In step S4, the so received output value is supplied as a result of the measuring routine to an I/O interface of the sensor chip.

While there are shown and described presently preferred embodiments of the invention, it is to be understood that the invention is not limited thereto but may be otherwise variously embodied and practised within the scope of the following claims.

The invention claimed is:

1. An integrated chemical sensor chip, comprising on or integrated in a common substrate
   a chemically sensitive layer,
   a heater for heating the sensitive layer,
   a memory for the storage of a measurement routine, the measurement routine comprising instructions defining a heating process over time and instructions defining one or more measurement points in time,
   an I/O interface for receiving a trigger for the measurement routine and for supplying a result of the measurement routine, and
   an engine for controlling the heater and for measuring a resistance of the sensitive layer according to instructions of the measurement routine in response to receiving a trigger for the measurement routine, wherein the engine is electrically interconnected with the sensitive layer and the heater on or in the substrate in an integrated circuit through which the engine receives a trigger as aforesaid and executes heating of the heater and taking measurements of the resistance of the sensitive layer.

2. The integrated chemical sensor chip of claim 1, wherein the measurement routine is stored in the memory in form of a macro.

3. The integrated chemical sensor chip of claim 1, wherein different measurement routines are stored in the memory.

4. The integrated chemical sensor chip of claim 1, wherein the engine comprises a state machine.

5. The integrated chemical sensor chip of claim 1, wherein the engine is hardwired in the integrated chemical sensor chip.

6. The integrated chemical sensor chip of claim 1, comprising
a system controller configured to copy the instructions of the measurement routine from the memory to the engine for controlling the heater and for measuring the resistance, and in particular to copy the instructions of the measurement routine from the memory to the engine in response to interrupts requested from the engine.

7. The integrated chemical sensor chip of claim 1, wherein the memory is a one-time programmable on-chip memory.

8. Portable electronic device, comprising
an integrated chemical sensor chip according to claim 1,
a processing unit,
wherein the processing unit comprises an I/O interface for communicating with the integrated chemical sensor chip,
wherein the processing unit is configured to send a trigger for a measurement routine via the I/O interface to the integrated chemical sensor chip, and is configured to receive a result of the measurement routine via the I/O interface.

9. The portable electronic device of claim 8, wherein the processing unit is a non-real-time processing unit.

10. The portable electronic device of claim 8, comprising a common housing for the integrated chemical sensor chip and the processing unit.

11. The portable electronic device of claim 8, comprising a common carrier for the chemical sensor chip and the processing unit.

12. The portable electronic device of claim 8, which is one of one of a mobile phone, a handheld computer, an electronic reader, a tablet computer, a game controller, a pointing device, a photo or a video camera, a digital music player, an electronic wrist watch, a personal health tracking device, a headset, or a computer peripheral.

* * * * *